(12) United States Patent
Weber et al.

(10) Patent No.: US 7,758,572 B2
(45) Date of Patent: Jul. 20, 2010

(54) MEDICAL DEVICES AND METHODS INCLUDING COOLING BALLOONS HAVING NANOTUBES

(75) Inventors: Jan Weber, Maple Grove, MN (US); John M. Hokanson, Maple Grove, MN (US); John J. Chen, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 308 days.

(21) Appl. No.: 10/850,087

(22) Filed: May 20, 2004

(65) Prior Publication Data

US 2005/0261670 A1 Nov. 24, 2005

(51) Int. Cl.
*A61B 18/18* (2006.01)
*A61M 29/00* (2006.01)

(52) U.S. Cl. ............... 606/23; 606/192; 604/103.06
(58) Field of Classification Search ............ 606/20–26, 606/192–194; 604/96.01–104
See application file for complete search history.

(56) References Cited

U.S. PATENT DOCUMENTS

| | | | |
|---|---|---|---|
| 4,955,377 A | 9/1990 | Lennox et al. | |
| 4,963,313 A | 10/1990 | Noddin et al. | |
| 5,122,137 A | 6/1992 | Lennox | |
| 5,270,086 A | 12/1993 | Hamlin | |
| 5,486,208 A | 1/1996 | Ginsburg | |
| 5,714,110 A | 2/1998 | Wang et al. | |
| 5,772,681 A * | 6/1998 | Leoni | 606/192 |
| 5,868,735 A * | 2/1999 | Lafontaine | 606/21 |
| 5,915,969 A | 6/1999 | Linden | |
| 6,120,364 A | 9/2000 | Laflamme | |
| 6,406,457 B1 | 6/2002 | Wang et al. | |
| 6,428,534 B1 | 8/2002 | Joye et al. | |
| 6,537,271 B1 | 3/2003 | Murray et al. | |
| 6,648,878 B2 * | 11/2003 | Lafontaine | 606/21 |
| 6,969,761 B2 * | 11/2005 | Mirkin et al. | 536/23.1 |
| 2002/0045894 A1 * | 4/2002 | Joye et al. | 606/21 |
| 2002/0156469 A1 | 10/2002 | Yon et al. | |
| 2003/0065355 A1 | 4/2003 | Weber | |
| 2003/0093107 A1 * | 5/2003 | Parsonage et al. | 606/194 |

(Continued)

FOREIGN PATENT DOCUMENTS

EP 1 388 346 A1 2/2004

(Continued)

OTHER PUBLICATIONS

William Bertoloni et al., "Medical Balloon," U.S. Appl. No. 10/263,225, filed Oct. 2, 2002.

(Continued)

*Primary Examiner*—Michael Peffley
(74) *Attorney, Agent, or Firm*—Crompton, Seager & Tufte, LLC (57) ABSTRACT

Medical systems and methods including balloons having nanotubes are disclosed. In some embodiments, a medical system includes an elongated shaft, and an expandable balloon carried by the shaft and including nanotubes. The medical system is capable of cooling the balloon to less than about 37° C. In some embodiments, a method includes providing a medical device having an elongated shaft, and an expandable balloon carried by the elongated shaft and including nanotubes; and cooling the balloon to less than about 37° C.

24 Claims, 5 Drawing Sheets

U.S. PATENT DOCUMENTS

| | | | | |
|---|---|---|---|---|
| 2003/0099798 | A1* | 5/2003 | George et al. | 428/36.9 |
| 2003/0143350 | A1* | 7/2003 | Jimenez | 428/35.2 |
| 2003/0229184 | A1* | 12/2003 | Acquarulo et al. | 525/505 |
| 2004/0073251 | A1 | 4/2004 | Weber | |
| 2005/0015046 | A1 | 1/2005 | Weber et al. | |
| 2005/0167647 | A1* | 8/2005 | Huang et al. | 257/14 |
| 2005/0238810 | A1* | 10/2005 | Scaringe et al. | 427/249.1 |
| 2005/0260355 | A1 | 11/2005 | Weber et al. | |
| 2005/0260412 | A1* | 11/2005 | Gardner | 428/408 |

FOREIGN PATENT DOCUMENTS

| | | |
|---|---|---|
| EP | 1388346 | 2/2004 |
| WO | 03/078317 | 9/2003 |
| WO | 2004/060472 | 7/2004 |
| WO | WO 2004/060472 A1 | 7/2004 |

OTHER PUBLICATIONS

Douglas A. Devens Jr., et al., "Multilayer Medical Devices," U.S. Appl. No. 10/645,014, filed Aug. 21, 2003.

Douglas A. Devens Jr., et al., "Medical Balloons," U.S. Appl. No. 10/645,055, filed Aug. 21, 2003.

Bronikowski et al., J. Vas Sci Technol A, 2001, 19(4), p. 1800-1805.

Davis et al., Macromolecules, 2004, 37, p. 154-160.

Bahr et al., J Am Chem Soc, 2001, 123, p. 6536-6542.

Krasheninnikov et al., Phys Rev B, 2002, 66, p. 245403.

Krasheninnikov et al., Phys Rev B, 2002, 65, p. 165423.

Biercuk et al., Applied Physics Letters, 2002, 80, p. 2767.

Cooper et al., Proceedings of the $8^{th}$ Annual Global Plastics Environ Conf, Feb 14, 2002, Soc of Plastics Engineers.

Choi et al., J of Applied Physics, Nov. 2003, 94(9), p. 6034-6039.

Ko et al., Adv Mater 2003, 15, No. 14, Jul. 17, p. 1161-1165.

Ashraf Abd El-Fattah Ali, "Carbon Nanotube Reinforced Carbon Nano Composite Fibrils by Electro-Spinning," Thesis, Drexel University, Oct. 2002.

International Search Report received in International Application No. PCT/US2005/017635, mailed Aug. 5, 2005.

Meador, Michael A., "UV Curable Polymers," Glenn Research Center, New Directions in High Performance Polymers, Hampton, VA, Apr. 26-27, 2001, 20 sheets.

U.S. Appl. No. 10/849,742 to John Jianhua Chen et al., filed May 20, 2004, entitled "Medical Devices Having Multiple Layers".

* cited by examiner

MEDICAL DEVICES AND METHODS INCLUDING COOLING BALLOONS HAVING NANOTUBES

TECHNICAL FIELD

The invention relates to medical devices.

BACKGROUND

The body includes various passageways such as arteries, other blood vessels, and other body lumens. These passageways, such as a coronary artery, sometimes become constricted or blocked, for example, by plaque or by a tumor. When this occurs, the constricted passageway can be widened in an angioplasty procedure using a balloon catheter, which includes a medical balloon carried by a catheter shaft.

In an angioplasty procedure, the balloon catheter can be used to treat a stenosis, or a narrowing of the body vessel, by collapsing the balloon and delivering it to a region of the vessel that has been narrowed to such a degree that fluid (e.g., blood) flow is restricted. The balloon can be delivered to a target site by passing the catheter shaft over an emplaced guidewire and advancing the catheter to the site. In some cases, the path to the site can be rather tortuous and/or narrow. Upon reaching the site, the balloon is then expanded, e.g., by injecting a fluid into the interior of the balloon. Expanding the balloon can expand the stenosis radially so that the vessel can permit an acceptable rate of fluid flow. After use, the balloon is collapsed, and the catheter is withdrawn.

In some cases, re-stenosis, which is the re-narrowing of the vessel, can occur after an angioplasty procedure. To reduce the occurrence of re-stenosis, the treatment site can be treated with, for example, prolonged balloon inflation, a heated balloon, a cooled balloon, radiation, drugs, and/or a stent.

SUMMARY

In one aspect, the invention features medical devices, such as cryogenic balloon catheters or heating balloon catheters, including nanotubes, such as carbon nanotubes. The nanotubes are capable of enhancing the thermal conductivity of the medical devices. In some embodiments, the nanotubes are incorporated in a polymer matrix, e.g., to form a composite, and the nanotubes can enhance the mechanical properties of the composite. Thus, the medical devices are capable of providing good heat transfer and good flexibility, which facilitates navigating the devices through the body.

In another aspect, the invention features a medical system, including an elongated shaft and an expandable balloon carried by the shaft, the balloon having nanotubes, wherein the medical system is capable of cooling the balloon to less than about 37° C.

In another aspect, the invention features a medical system, including an elongated shaft and an expandable balloon carried by the shaft, the balloon having nanotubes, wherein the medical system is capable of heating the balloon to greater than about 37° C.

In another aspect, the invention features a method, including providing a medical device having an elongated shaft and an expandable balloon carried by the elongated shaft, the balloon having nanotubes, and cooling the balloon to less than about 37° C. The method can include cooling the balloon to less than about 0° C. The method can further include contacting the balloon to a body vessel.

In another aspect, the invention features a method, including providing a medical device having an elongated shaft and an expandable balloon carried by the elongated shaft, the balloon having nanotubes, and heating the balloon to greater than about 37° C.

In another aspect, the invention features a medical device, including an elongated flexible shaft for delivery into a body lumen, and a tissue heater at a distal portion of the shaft, the heater including nanotubes. The heater can be capable of being heated resistively. The device can further include a fluid supply capable of heating the heater with a fluid at greater than about 37° C.

In another aspect, the invention features a medical device, including an elongated flexible shaft for delivery into a body lumen, the shaft having a portion including nanotubes, and a fluid supply capable of cooling the portion of the shaft with a fluid at less than about 37° C. The portion can be a distal portion.

Embodiments of the aspects may include one or more of the following features. The nanotubes include carbon nanotubes, such as single walled carbon nanotubes. The balloon includes a blend comprising a polymer and the nanotubes, such as from about 1% to about 50% by weight of the nanotubes. The nanotubes are functionalized. The nanotubes are aligned, e.g., by a magnetic field. The nanotubes are crosslinked. The nanotubes extend from an inner surface of the balloon and/or from an outer surface of the balloon. The system is capable of cooling or cooling an interior surface of the balloon and/or an exterior surface of the balloon. The system further includes a second expandable balloon surrounding the expandable balloon.

In another aspect, the invention features a medical device including a catheter having a distal end and a proximal end, a balloon at the distal end and having nanotubes, a heating source or a cooling source at the proximal end, and a conductor for carrying heat or cold from the heating source or the cooling source to the balloon.

Embodiments may have one or more of the following advantages. Treating the treatment site with heat and/or cold can reduce the occurrence of restenosis, particularly where use of a stent is not practical, such as in peripheral applications. Since thermal transfer is enhanced, the treatment site can be cooled and heated more quickly, thereby reducing the treatment time and/or adverse effect from a prolonged medical procedure. In some embodiments, the nanotubes can enhance the physical properties, e.g., strength, of the devices.

Other aspects, features, and advantages of the invention will be apparent from the description of the preferred embodiments thereof and from the claims.

DETAILED DESCRIPTION

Figure 1:
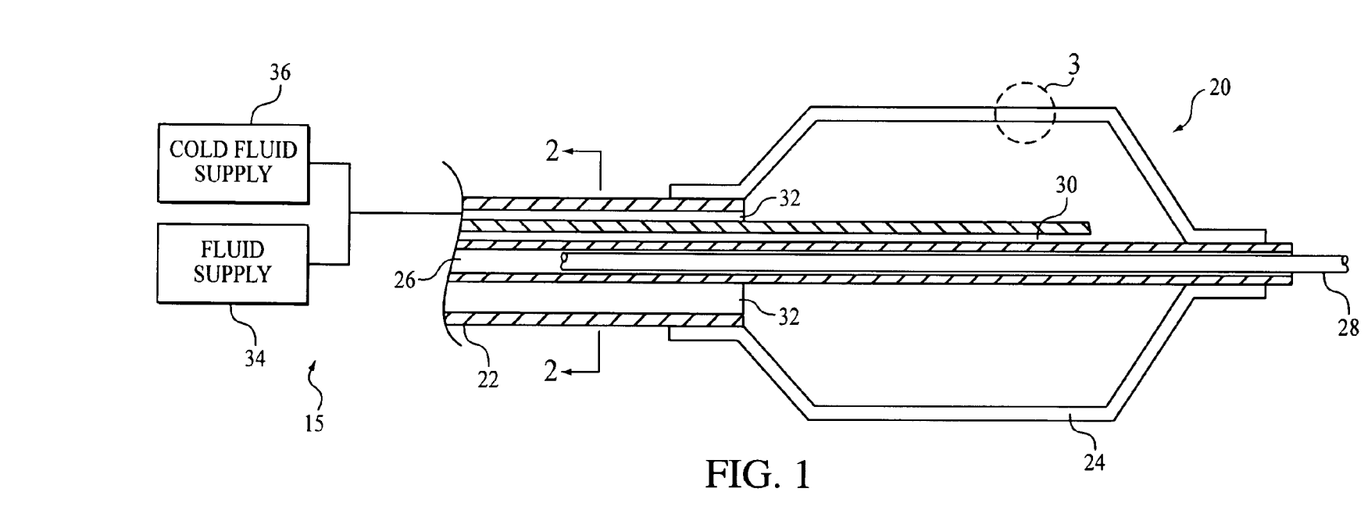
FIG. 1 is an illustration of a balloon catheter system including a longitudinal cross-section of a portion of a balloon catheter.
Figure 2:
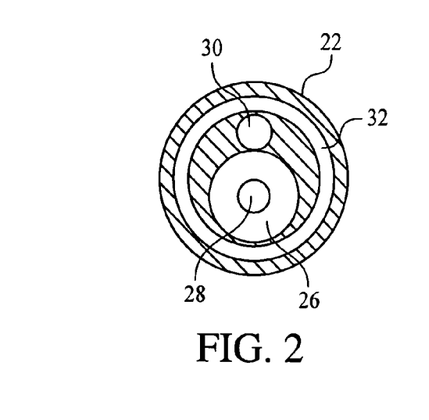
FIG. 2 is a cross-sectional view of the balloon catheter of FIG. 1, taken along line 2-2.

Referring to FIGS. 1 and 2, a balloon catheter system 15 includes a balloon catheter 20 having an elongated catheter shaft 22 constructed for delivery into a body vessel, and an expandable balloon 24 carried by a distal portion of the catheter shaft. Catheter shaft 22 includes a guidewire lumen 26 for passing balloon catheter 20 over an emplaced guidewire 28. Catheter shaft 22 further includes an inflation lumen 30 and an exhaust lumen 32, both of which are in fluid communication with the interior of balloon 24. As shown, inflation lumen 30 is also in fluid communication with a fluid supply 34 and a cold fluid supply 36. Other balloon catheter systems are described, for example, in Wang, U.S. Pat. No. 5,915,969; Hamlin, U.S. Pat. No. 5,270,086; and Lennox U.S. Pat. No. 6,428,534. In some embodiments, for example, the catheter shaft can include concentric lumens.

During use, fluid is introduced through inflation lumen 30 and into the interior of balloon 24. For example, to widen an occluded treatment site in a body vessel during an angioplasty procedure, balloon 24 can be expanded at the site by introducing the fluid through inflation lumen 30 into the balloon at a rate faster than the rate at which the fluid exits the balloon through exhaust lumen 32, thereby radially expanding the vessel until the balloon is fully expanded and a steady state flow is maintained by a difference in pressure between fluid entering the balloon and fluid exiting the balloon. Prior to and/or subsequent to expanding the body vessel, the occluded site can be treated with a cooled balloon, e.g., to reduce the occurrence of restenosis. Cold fluid from cold fluid supply 36 can be delivered through inflation lumen 30 at a sufficient pressure to expand balloon 24 and to contact the cold balloon against the body vessel.

Figure 3:
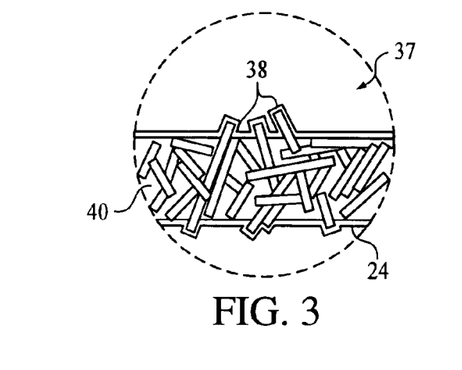
FIG. 3 is an illustration of a portion of the balloon catheter of FIG. 1.

Referring further to FIG. 3, balloon 24 is constructed to enhance heat transfer between the fluid in the balloon and the body vessel. As shown, balloon 24 is formed of a mixture 37 including nanotubes 38, such as carbon nanotubes, and a polymer 40. Polymer 40 serves as a matrix material that provides balloon 24 with resiliency and flexibility so that the balloon can be navigated through the tortuous path to the treatment site, inflated and deflated. Nanotubes 38 provide mixture 37 with good thermal conductivity, e.g., relative to polymer 40, without substantially adversely affecting flexibility. For example, in some embodiments, a mixture having a first polymer and single wall carbon nanotubes can have a thermal conductivity from about 70% to about 125% higher than the thermal conductivity of the first polymer, depending on the temperature. As a result, heat transfer through balloon 24 is facilitated. In a procedure in which cold fluid is introduced into balloon 24, the treatment site can be cooled more quickly, which consequently reduces the time for the procedure and reduces any adverse effect from a prolonged medical procedure. Furthermore, since the thermal conductivity of the balloon is increased, heat resistance through the balloon is reduced and the temperature to which the body vessel is exposed more closely matches the temperature of the cold fluid introduced into the balloon. In comparison, where the thermal conductivity of the balloon is low, the temperature of the fluid may need to be adjusted to compensate for the high resistance to heat transfer through the relatively poorly conducting balloon and/or the relatively prolonged procedure.

Moreover, in addition to enhancing thermal conductivity, nanotubes 38 can also enhance the physical properties, such as strength, toughness, elasticity, and/or durability, of polymer 40. As a result, balloon 24 can be made with a thinner wall thickness, without compromising, for example, burst strength and pinhole resistance. For example, in some embodiments, a nanotube-containing polymer composite can have an ultimate strength about twice as high as the ultimate strength of the pure polymer. As a result, to maintain about the same ultimate strength, the thickness of a structure including the nanotube-containing polymer can be reduced by about 50% (e.g., reduced by less than about 40%, 30%, 20%, or 10%) relative to the thickness of a structure including the pure polymer. The thermal resistance of the wall is reduced both by increasing the thermal conductivity and by reducing the wall thickness. The reduced wall thickness, in turn, reduces the profile of the balloon, thereby increasing its flexibility to navigate a tortuous path and accessibility to relatively narrow body vessels.

In some embodiments, the nanotubes are on or near the inner surface and/or the outer surface of the balloon to enhance thermal transfer. For example, the nanotubes can extend from a surface, and/or the nanotubes can be less than several (e.g., about one or less) nanotube thickness from a surface. Across the cross-sectional thickness of the balloon wall, the nanotubes can be in close proximity (e.g., contacting) relative to each other. Certain nanotubes can span the thickness of the balloon wall.

Nanotubes 38 include particles having at least one dimension less than about 1000 nm. Examples of nanotubes include hollow carbon nanotubes, such as hollow single walled carbon nanotubes and hollow multiwalled carbon nanotubes (sometimes called buckytubes); ceramic nanotubes such as boron nitride nanotubes and aluminum nitride nanotubes; and metallic nanotubes such as gold nanotubes. Certain carbon nanotubes, for example, can conduct heat as good as or better than diamond, and can conduct electricity similar to metals. Carbon nanotubes are available from, for example, Rice University, and Carbon Nanotechnologies Inc. (CNI) (Houston, Tex.). Synthesis of carbon nanotubes is described, for example, in Bronikowski et al., *J. Vac. Sci. Technol.* A, 19(4), 1800-1805 (2001); and Davis et al., *Macromolecules* 2004, 37, 154-160. Boron nitride nanotubes are available from The Australian National University (Canberra, Australia). More than one type of nanotubes can be included in mixture 37.

The physical dimensions of nanotubes 38 can be expressed as units of length and/or as a length to width aspect ratio. Nanotubes 38 can have an average length of from about 0.1 micron to about 20 microns. For example, the length can be greater than or equal to about 0.1 micron, 0.5 micron, 1 micron, 5 microns, 10 microns, or 15 microns; and/or less than or equal to about 20 microns, 15 microns, 10 microns, 5 microns, 1 micron, or 0.5 micron. Nanotubes 38 can have an average width or diameter of from about 0.5 nm to about 150 nm. For example, the width or diameter can be greater than or equal to about 0.5 nm, 1 nm, 5 nm, 10 nm, 25 nm, 50 nm, 75 nm, 100 nm, or 125 nm; and/or less than or equal to about 150 nm, 125 nm, 100 nm, 75 nm, 50 nm, 25 nm, 10 nm, 5 nm, or 1 nm. Alternatively or in addition, nanotubes 38 can be expressed as having a length to width aspect ratio of from about 10:1 to about 50,000:1. The length to width aspect ratio can be greater than or equal to about 10:1, 100:1, or 1,000:1; 2,500:1; 5,000:1; 10,000:1; 20,000:1; 30,000:1; or 40,000:1;

and/or less than or equal to about 50,000:1; 40,000:1; 30,000:1; 20,000:1; 10,000:1; 5,000:1; 2,500:1; 1,000:1, or 100:1. The nanotubes preferably have long lengths and small diameters. In some embodiments, the length of the nanotubes is as long as or longer than the thickness of the wall of the balloon.

The concentration of nanotubes 38 in mixture 37 can be a function of, for example, the specific composition of the nanotubes, the dimensions of the nanotubes, the composition of polymer 40, and/or the targeted thermal conductivity. In some embodiments, mixture 37 includes from about 0.5% to about 50% by weight of nanotubes 38. For example, mixture 37 can include, by weight, greater than or equal to about 0.5%, 1%, 5%, 10%, 15%, 20%, 25%, 30%, 35%, 40%, or 45% of nanotubes; and/or less than or equal to about 50%, 45%, 40%, 35%, 30%, 25%, 20%, 15%, 10%, 5%, or 1% of nanotubes.

In some embodiments, nanotubes 38 are modified to enhance interactions among the nanotubes and/or interactions between the nanotubes and polymer 40. Nanotubes 38 can be chemically modified with one or more functional groups that increase interactions (e.g., compatibility) with polymer 40. Functionalization of carbon nanotubes are described, for example, in Bahr et al., *J. Am. Chem. Soc.* 2001, 123, 6536-6542, and U.S. Patent Application Publication 2003/0093107. Alternatively or in addition, nanotubes 38 can be connected or crosslinked, for example, by irradiation. Irradiation of carbon nanotubes are described, for example, in Krasheninnikov et al., *Phys. Rev. B* 66, 245403 (2002); Krasheninnikov et al., *Phys. Rev. B* 65 (2002) 165423; and commonly assigned U.S. Ser. No. 10/850,085, filed concurrently with this application.

Polymer 40 can include, for example, thermoplastics and thermosets. Examples of thermoplastics include polyolefins, polyamides, such as nylon 12, nylon 11, nylon 6/12, nylon 6, and nylon 66, polyesters (such as polyethylene terephthalate (PET)), polyethers, polyurethanes, polyvinyls, polyacrylics, fluoropolymers, copolymers and block copolymers thereof, such as block copolymers of polyether and polyamide, e.g., Pebax®; and mixtures thereof. Examples of thermosets include elastomers such as EPDM, epichlorohydrin, polyureas, nitrile butadiene elastomers, silicones, etc. Thermosets, such as expoxies and isocyanates, can also be used. Biocompatible thermosets may also be used, and these include, for example, biodegradable polycaprolactone, poly (dimethylsiloxane) containing polyurethanes and ureas, and polysiloxanes. Ultraviolet curable polymers, such as polyimides, can also be used. Other polymers are described in commonly assigned U.S. Ser. No. 10/645,055, filed Aug. 21, 2003. Mixture 37 can include one or more polymers 40.

In addition to nanotubes 38 and polymer 40, mixture 37 can further include one or more additives that enhance formation of a composite. For example, mixture 37 can include one or more coupling or compatibilizing agents, dispersants, stabilizers, plasticizers, surfactants, and/or pigments, that enhance interactions between the nanotubes and the polymer. Examples of additive(s) are described in U.S. Patent Application Publication 2003/0093107.

Mixture 37 can be formed by combining nanotubes 38, polymer 40, and optionally, one or more additives, and processing the combination using composite-forming techniques. Methods of making nanotube-containing mixtures are described, for example, in Biercuk, et al., *Applied Physics Letters*, 80, 2767 (2002). The combination can be blow molded, film molded, injection molded, and/or extruded. Examples of method of making medical tubing using composite-forming techniques are described in U.S. Patent Application Publication 2003/0093107. Methods of forming a balloon from a tube are described in, for example, commonly-assigned U.S. Ser. No. 10/263,225, filed Oct. 2, 2002, and entitled "Medical Balloon"; Anderson U.S. Pat. No. 6,120, 364; Wang U.S. Pat. No. 5,714,110; and Noddin U.S. Pat. No. 4,963,313, all hereby incorporated by reference in their entirety. The balloon can be attached to catheter shaft 22, for example, by laser bonding. Catheter shaft 22 may also be any of the multilayer tubes described in commonly assigned U.S. Ser. No. 10/645,014, filed Aug. 21, 2003. In some embodiments, catheter shaft 22 includes nanotubes.

Figure 4:
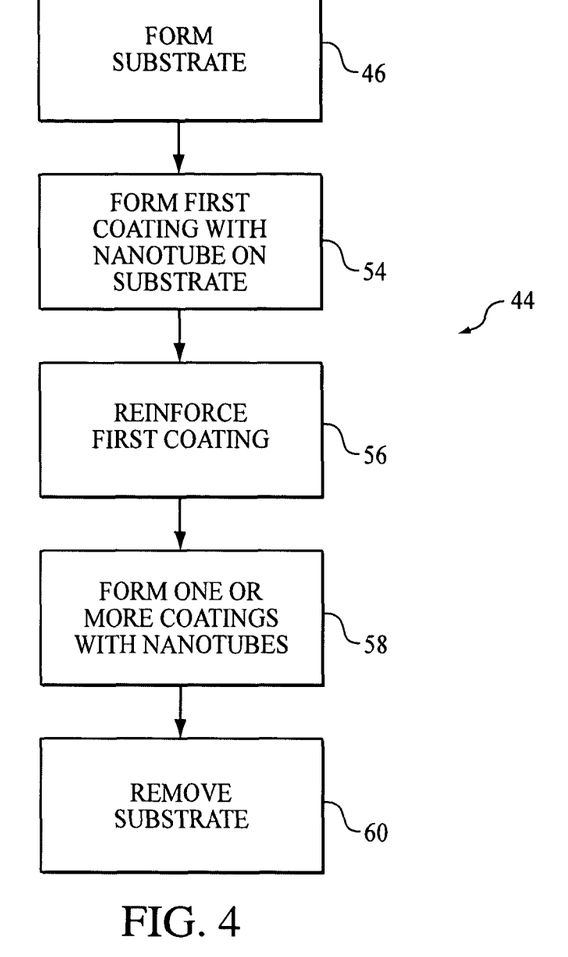
FIG. 4 is a flow chart of a method of a making a medical balloon.

In other embodiments, balloon 24 can be formed by depositing nanotubes 38 on a substrate, and subsequently removing the substrate. Referring to FIG. 4, a method 44 of making balloon 24 includes providing a removable substrate in the shape of the balloon (step 46). For example, referring to FIG. 5, a substrate 48 can be formed by molding (e.g., injection molding) a degradable or dissolvable material, such as polyvinyl alcohol (PVOH), into the shape slightly smaller than balloon 24. As shown, substrate 48 has a longitudinal lumen 50 and an outer surface with a helically extending groove 52. Lumen 50 allows a material, such as hot water, to be flushed through substrate 48 to remove the substrate material. As described below, groove 52 allows a reinforcement material to extend around the balloon. Alternatively or in addition, the outer surface of substrate 48 can be textured (e.g., dimpled) or roughened to increase the surface area available for the nanotubes to be deposited. Degradable polyvinyl alcohol is described, for example, in Cooper et al., *Proceedings of the 8th Annual Global Plastics Environmental Conference*, Society of Plastics Engineers, Detroit Mich., 360, 14 Feb. 2002. In some embodiments, the substrate material, such as PVOH, includes nanotubes, for example, about 0.5% to about 70%, e.g., about 0.5-50%, or 0.5-10%, of nanotubes by weight.

Referring again to FIG. 4, next, a layer containing nanotubes 48 is formed on substrate 48 (step 54). Nanotubes 48 can be dispersed in a mixture, such as 1,1,2,2-tetrachloroethane (available from Zyvex) and polyurethane (available from Estane). Nanotubes 38 can be deposited on substrate 48 by spraying the nanotube mixture onto the substrate or by dip coating the substrate into the mixture to form a first coating on the substrate. In some embodiments, a mixture containing nanotubes 38 and 1,1,2,2-tetrachloroethane is applied to substrate 48 first, followed by application of the mixture containing the nanotubes, 1,1,2,2-tetrachloroethane, and polyurethane. As a result, a layer of nanotubes, sometimes called bucky paper, can be formed as an interior surface of the balloon to enhance thermal conductivity. In other embodiments, nanotubes 38 can be mixed with a UV crosslinkable polymer, such as a polyimide or a polyester, as described in Meador, "UV Curable Polymers", New Directions in High Performance Polymers, Hampton Va., Apr. 26-27, 2001.

In some embodiments, while the mixture containing nanotubes 48 has sufficiently low viscosity, the mixture can be magnetically processed to align the nanotubes, which can enhance the thermal conductivity of the mixture. The nanotubes can be aligned or oriented due to the cooperative effect of the magnetic torque exerted by the magnetic field on the nanotubes and by the hydrodynamic torque and viscous shear exerted on the nanotubes by the polymer chains, which also respond to the field due to magnetic anisotropy, as described in Choi et al., *J. of Appl. Phys., Vol. 94*, No. 9, 1 Nov. 2003, 6034-6039. The nanotubes can be aligned, for example, by exposing them to up to 25 Tesla for about two to four hours at 25-60° C., as described in Choi et. al.

In embodiments in which substrate 48 includes nanotubes, an outer portion or layer of the substrate can be removed prior to forming the first coating on the substrate. For example, hot water can be used to remove a layer of PVOH to expose the nanotubes. The exposed nanotubes, which may randomly protrude radially from the substrate, can bond well with the first coating. In addition, when the substrate is completely removed (described below), the nanotubes are partially embedded in the balloon and partially exposed at the surface of the balloon, which provides a highly thermally conductive inner layer for the balloon. Alternatively or in addition, the balloon can be formed to include an outer layer having protruded or exposed nanotubes, as described below.

Figure 5:
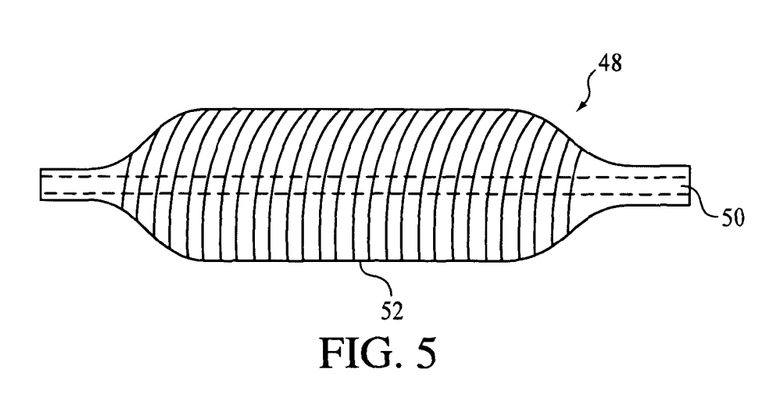
FIG. 5 is an illustration of a substrate for making a medical balloon.

To strengthen the first coating, a reinforcement layer can optionally be formed on the first coating (step 56). For example, fibers of stainless steel, carbon, or Kevlar™ can be wrapped around substrate 48 along groove 52. Alternatively or in addition, fibers containing nanotubes can be wrapped around the first coating. The fibers allow high loading (e.g., up to about 50% by weight) of nanotubes on the balloon. Nanotube-containing fibers can be formed, for example, by electrospinning, described in Ko et al., *Adv. Mater.* 2000, 15, No. 14, Jul. 17, 1161-1163; and "Carbon Nanotube Reinforced Carbon Nano Composite Fibrils By Electro-Spinning", thesis by Ashraf Abd El-Fattah Ali, Drexel University, October 2002.

Next, additional layer(s) including nanotubes 38 is formed by applying one or more applications of the nanotube mixture (step 58) until the desired thickness is achieved. To form an outer layer having nanotubes that are partially exposed and partially embedded in the balloon, a mixture containing PVOH and nanotubes can be sprayed onto a layer 38 before the layer has solidified to embed the nanotubes in the layer. Subsequently, the PVOH can be removed. e.g., with hot water.

Substrate 48 can be removed by flushing lumen 50 with the appropriate material, such as hot water (step 60), thereby leaving a balloon including nanotubes. Embodiments of the method described above are also described in U.S. Ser. No. 10/622,621, entitled "Medical Devices and Processes for Preparing Same".

Other methods of forming the balloon include forming a multilayer structure having a plurality of alternating, oppositely charged layers, as described in U.S. Ser. No. 10/849,742, entitled "Layer-by-Layer Assembly of Multilayer Regions for Medical Devices" and filed on the same day as this application. The structure can include, for example, a plurality of layers containing charged nanoparticles alternating with a plurality of layers containing charged polyelectrolytes. Charging can be provided, for example, using an electrical potential, by covalently attaching functional groups, and/or by exposing the layers to one or more charged amphiphilic substances. Exemplary materials and techniques are described in U.S. Ser. No. 10/849,742.

Figure 6:
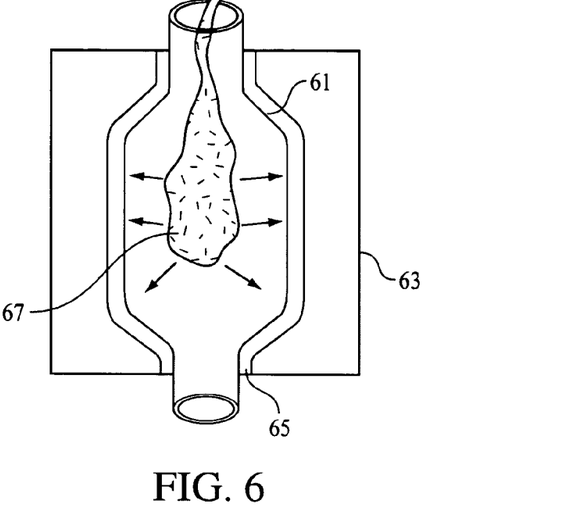
FIG. 6 is an illustration of an apparatus for making a medical balloon.

In other embodiments, a layer containing nanotubes can be formed by filtering a mixture containing the nanotubes through an appropriately shaped filter. Referring to FIG. 6, a filter 61 generally having the shape of a balloon and a shape constraint 65 (such as a mesh form) are placed in a vacuum chamber 63. Shape constraint 65 helps filter 61 to maintain its shape under vacuum. A mixture 67 containing nanotubes (such as the 1,1,2,2-tetrachloroethane mixture described above) is then introduced into filter 61, which is under vacuum. As a result, mixture 67 is filtered through filter 61 (arrows), thereby leaving a layer of nanotubes against the interior wall of the filter. One or more additional layers of nanotubes and/or polymer can be formed on the first layer of nanotubes; and/or the first layer of nanotubes can be reinforced as described above, in any combination. Filter 61 can be removed to provided the finished balloon. In other embodiments, a mixture containing nanotubes can be injected or sprayed under pressure against the wall of a balloon-shaped filter.

Referring again to FIG. 1, in use, balloon catheter 20 can be delivered to the treatment site by passing guidewire lumen 26 over an emplaced guidewire 28, and pushing the catheter to the treatment site. The treatment site can then be radially expanded by introducing fluid from fluid supply 34, through inflation lumen 30, and into the interior of balloon 24. Thereafter, the fluid can be removed through exhaust lumen 32 to deflate balloon 24.

Prior to and/or subsequent to radially expanding the treatment site, a cryogenic fluid (such as a liquid (e.g., cooled saline) or liquid/gas mixture including carbon dioxide or nitrous oxide) is introduced from cold fluid supply 36, through inflation lumen 30, and into the interior of balloon 24. The cryogenic fluid radially expands balloon 24 and contacts the cooled balloon against the body vessel, thereby cooling the vessel. In other embodiments, the cryogenic fluid can be used to radially expand and to cool the body vessel simultaneously in one step. Methods of cryogenically treating a body vessel are described in Joye et al., U.S. Pat. No. 6,428,534, and Joye et al., U.S. Patent Application Publication No. 2002/0045894.

Figure 7:
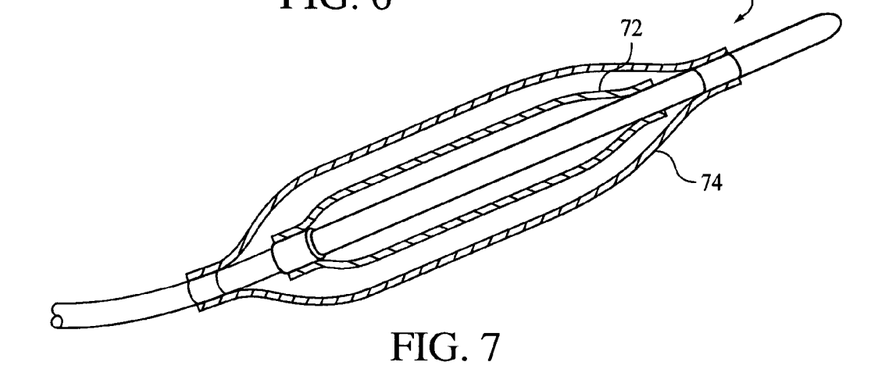
FIG. 7 is an illustration, along a longitudinal cross section, of a balloon catheter having an inner balloon and outer balloon.

In other embodiments, balloons of other balloon catheter systems can be formed to include nanotubes 38. Referring to FIG. 7, a balloon catheter 70 includes an inner balloon 72 and an outer balloon 74 over the inner balloon. Inner balloon 72 can be used for cryogenic treatment, and outer balloon 74 can be used for vessel dilation, as well to reduce leakage of cryogenic fluid into the body in case of inner balloon failure. Either balloon 72 or 74, or both balloons, can include nanotubes as described above. Embodiments of balloon catheter 70 and methods of using the balloon catheter are described in U.S. Patent Application Publication No. 2002/0045894.

Figure 8:
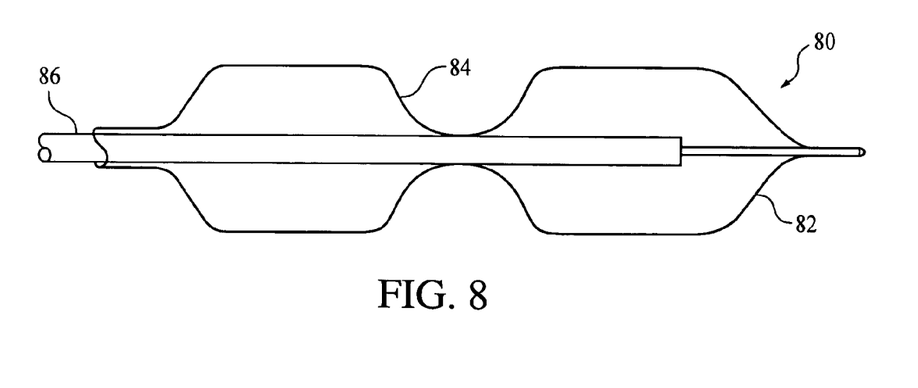
FIG. 8 is an illustration, along a longitudinal cross section, of a balloon catheter having a proximal balloon and a distal balloon.

Referring to FIG. 8, a balloon catheter 80 includes a distal balloon 82 and a proximal balloon 84, both carried by a catheter shaft 86. Distal balloon 82 can be used for vessel dilation, and proximal balloon 84 can be used for cryogenic treatment. Balloons 82 and 84 can be formed of the same composition or of different compositions, e.g., the distal balloon can include a compliant material, while the proximal balloon can include a non-compliant material. Either balloon 82 or 84, or both balloons can include nanotubes as described above. Embodiments of balloon catheter 80 and methods of using the balloon catheter are described in U.S. Pat. No. 6,428,534.

Figure 9:
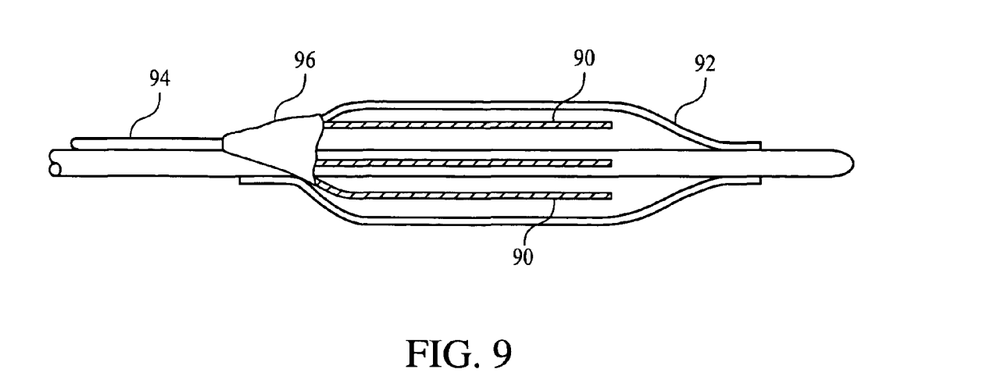
FIG. 9 is an illustration of a balloon catheter.

In some embodiments, nanotube-containing fibers, for example, made by electrospinning, can be placed on a medical balloon to enhance thermal conductivity. The balloon can be a conventional balloon or the balloon can include nanofibers as described above. The fibers can be wrapped, e.g., helically, about the balloon, and/or referring to FIG. 9, the fibers 90 can extend longitudinally along the length of the balloon 92. As shown in FIG. 9, the proximal ends of fibers 90 are connected to a hypotube 94, such as a metal wire insulated by a polymer. The proximal end of hypotube 94 can be submerged into a cryogenic fluid, such as liquid nitrogen, to further cool fibers 90 through conduction. As shown, fibers 90 are covered by polymer insulation 96 to reduce heat loss from hypotube 94 to portions of the fibers 90 on balloon 92.

Figure 10:
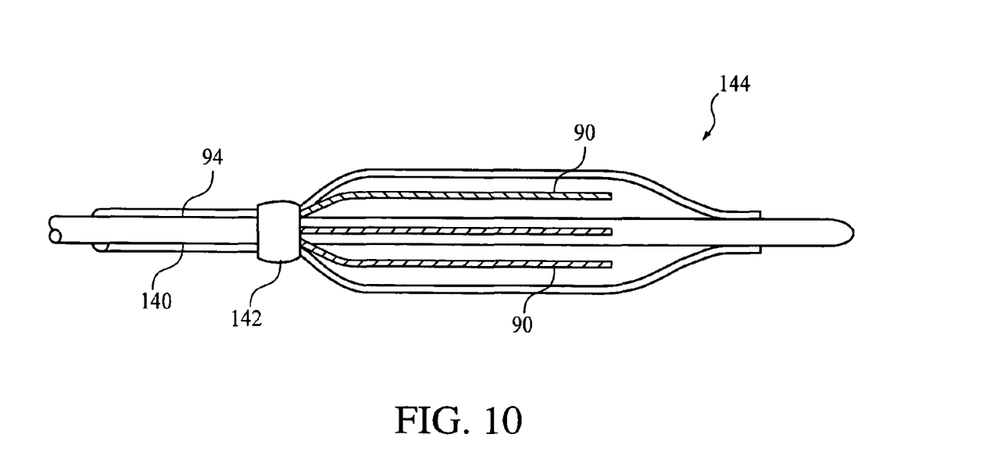
FIG. 10 is an illustration of a balloon catheter.

In other embodiments, referring to FIG. 10, fibers 90 can be in fluid communication with two hypotubes 94 and 140, and a reservoir 142. As shown, a balloon catheter 144 includes hypotubes 94 and 140 that are in fluid communication with reservoir 142 (e.g., an annular chamber that fits around the catheter shaft). Reservoir 142 is, in turn, in fluid communication with fibers 90. During use, fluid (e.g., a coolant) is passed through a first hypotube (e.g., hypotube 94), to reservoir 142 which distributes the fluid to fibers 90, and then passed through a second hypotube (e.g., hypotube 140). The fluid exiting proximally from the second hypotube can be cooled and recirculated back to the first hypotube, e.g., to form a closed loop of fluid flow. As shown, fibers 90 extend generally longitudinally along the balloon. Alternatively or in addition, fibers 90 can extend in other ways, such as helically.

The nanotube-containing balloons and the nanotube-containing mixtures described above can also be used in heating or hyperthermic medical devices.

Figure 11:
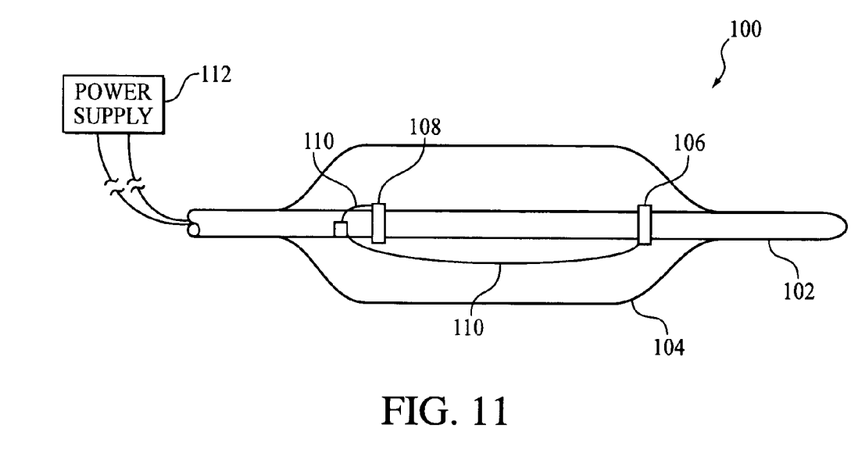
FIG. 11 is an illustration of a balloon catheter system including a longitudinal cross section of a balloon catheter.

Referring to FIG. 11, a balloon catheter 100 includes a catheter shaft 102 and a balloon 104 carried by the catheter shaft. Balloon catheter 100 further includes two annular electrical contacts 106 and 108 carried by shaft 102. Contacts 106 and 108 are connected to wires 110, which extend proximally within shaft 102 to a power supply 112. Power supply 112 is capable of flowing current between contacts 106 and 108, which consequently can heat inflation fluid in balloon 104. Balloon 104 and/or balloon catheter 100 can be formed according to any of the embodiments described above. As a result, the heat generated can be effectively transferred to a treatment site. The hyperthermal treatment can be used, e.g., to treat tumors, or to glaze or to smooth plaque from a vessel wall (e.g., by dehydration and compression), thereby enhancing vessel patency. Embodiments of balloon catheter 100 and methods of using the balloon catheter are described in Lennox et al., U.S. Pat. No. 4,955,377.

In some embodiments, the nanotubes can be incorporated only in selected portion(s) of a cooling balloon or a heating balloon. For example, the nanotubes can be incorporated only in the inflatable, tissue-contacting body portion of a balloon, but not in the tapered, conical regions or the sleeve regions that connect to the catheter shaft.

Figure 12:
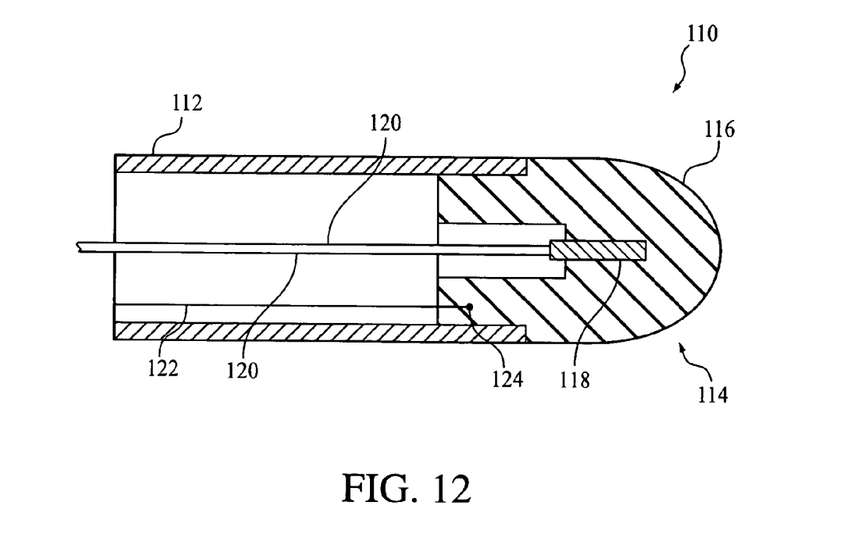
FIG. 12 is an illustration of a probe along a longitudinal cross section.

Nanotube-containing mixture 37 described above can be applied to medical devices capable of heating tissue, e.g., to induce coagulation. Referring to FIG. 12, a radiofrequency (RF) probe 110 includes a shaft 112 having an RF tip 114. Tip 114 includes an electrode portion 116, and a thermistor assembly 118 embedded in the electrode portion. Thermistor assembly 118, which is connected to a pair of leads 120, is capable of sensing the temperature of electrode portion 116 as an indirect indication of the temperature of tissue surrounding the electrode. A single RF electrode lead 122 connects with electrode portion 116 at resistance weld 124. During use, an RF electrical current is applied from probe 110 to pass through body tissue to locally heat the tissue. In preferred embodiments, electrode portion 116 includes (e.g., is formed of) nanotube-containing mixture 37 described above to enhance heat transfer and electrical conductance between probe 110 and surrounding tissue. In addition, since heat resistance through electrode portion 116 is relatively low, the temperature sensed by thermistor assembly 118 more accurately indicates the temperature of the surrounding tissue, e.g., relative to other nonmetallic materials. The relatively soft tip provided by mixture 37 can also reduce the occurrence of injury from a relatively harder tip. Embodiments of heating devices, such as RF probes, guidewire probes, forceps devices, and catheters, methods of using the heating devices are described in Lennox, et al., U.S. Pat. No. 5,122,137.

Still other hypothermic and hyperthermic devices can include nanotubes for enhanced thermal conductivity. Examples of such devices include a catheter shaft having, at the distal portion of the shaft, a heatable element and/or a structure that can be cooled or heated, as described, for example, in Ginsburg, U.S. Pat. No. 5,486,208. The distal portion of the catheter shaft can be formed of a composite including a polymer and nanotubes for good thermal conductivity.

The following example is illustrative and not intended to be limiting.

EXAMPLE

This example describes a method of making a tube including a composite of carbon nanotubes and a polymer. The polymer was Pebax 7233 from AtoFina, Philadelphia, Pa. and the carbon nanotubes were MB4220, a PA 12 based carbon nanotube master batch from Hyperion Catalysis International, Cambridge, Mass. The carbon nanotube content was 20%.

The Pebax 7233 polymer and the MB4220 nanotubes were hand mixed at 3:1 ratio by weight, respectively.

Next, the materials were compounded. The compounding equipment included a ThermoHaake Polylab system, which includes an instrumented drive system, a 16 mm co-rotating twin screw extruder, and downstream quenching and pelletizing equipment. Pellets were fed into the extruder using a Ktron loss in weight feeder. The aggressive mixing screw was used in the compounding process. The mixture was fed at 24 g/minute. The screw speed was 250 rpm. The melt temperature was about 237° C.

These compounded pellets were used for tubing extrusion. The tubing size was 0.0355 I.D.×0.0605 O.D. A 0.75-inch Brabender extruder was used for tubing extrusion. The barrel temperatures were 360/385/400 F and the die temperature was 410 F. The extrusion line was equipped with 0.16 cc-melt pump at 45 rpm and 55 microns melt filter. The area draw down ratio was 8.68.

All publications, applications, patents, and references referred to in this application are herein incorporated by reference in their entirety.

Other embodiments are within the claims.

What is claimed is:

1. A medical system, comprising:
an elongated shaft and an expandable balloon carried by the shaft, the balloon having a balloon wall region having an inner surface and an outer surface, the balloon wall region comprising an inner layer containing carbon nanotubes, a helical reinforcement layer disposed over the first layer and an outer layer disposed over the reinforcement layer comprising a mixture comprising a polymeric material and single wall carbon nanotube particles, at least some of which extend from the inner surface and/or from the outer surface, the mixture having a thermal conductivity of from about 70 percent to about 125 percent higher than the thermal conductivity of the polymeric material, and
a hypotube having a proximal end and a distal end, the hypotube extending along the elongated shaft;
one or more fibers each having a proximal end and a distal end, the one or more fibers extending longitudinally along an outer surface of the balloon, wherein the proximal ends of the one or more fibers are attached to the distal end of the hypotube; and
the medical system being capable of cooling the balloon wall region of the balloon to less than about 37° C.

2. The system of claim 1, wherein the mixture comprises from about 1% to about 50% by weight of the single wall carbon nanotube particles.

3. The system of claim 1, wherein the single wall carbon nanotube particles are functionalized.

4. The system of claim 1, wherein the single wall carbon nanotube particles are crosslinked.

5. The system of claim 1, wherein the single wall carbon nanotube particles are aligned in a predetermined direction in the mixture.

6. The system of claim 1, wherein the system is capable of cooling the inner surface of the balloon wall region.

7. The system of claim 1, wherein the system is capable of cooling the exterior surface of the balloon wall region.

8. The system of claim 1, further comprising a second expandable balloon surrounding the expandable balloon.

9. The system of claim 1, wherein the polymeric material comprises a thermoset.

10. The system of claim 1, wherein the polymeric material comprises a thermoplastic.

11. The system of claim 1, wherein the polymeric material is selected from the group consisting of polyolefins, polyamides, polyesters, polyethers, polyurethanes, polyvinyls, polyacrylics, fluoropolymers, copolymers and block copolymers thereof, and mixtures thereof.

12. The system of claim 1, wherein at least some the nanotube particles contact other nanotube particles across a cross-sectional thickness of the balloon wall region.

13. The system of claim 1, wherein the one or more fibers are spaced about the circumference of the balloon.

14. The system of claim 1, wherein the one or more fibers include nanoparticles.

15. The system of claim 14, wherein the one or more fibers include single wall carbon nanotubes.

16. The system of claim 1, further including a polymer disposed over proximal ends of the one or more fibers where the one or more fibers are attached to the hypotube.

17. A method, comprising:
providing a medical device comprising an elongated shaft and an expandable balloon carried by the elongated shaft, the balloon having a balloon wall region having an inner and an outer surface, the balloon wall region comprising an inner layer containing carbon nanotubes, a helical reinforcement layer disposed over the first layer and an outer layer disposed over the reinforcement layer comprising a mixture comprising a polymeric material and single wall carbon nanotube particles, at least some of which extend from the inner surface and/or from the outer surface, the mixture having a thermal conductivity of from about 70 percent to about 125 percent higher than the thermal conductivity of the polymeric material, the medical device further including a hypotube having a proximal end and a distal end, the hypotube extending along the elongated shaft and one or more fibers each having a proximal end and a distal end, the one or more fibers extending longitudinally along an outer surface of the balloon, wherein the proximal ends of the one or more fibers are attached to the distal end of the hypotube;
submerging the proximal end of the hypotube into a cryogenic fluid; and
cooling the balloon wall region to less than about 37° C.

18. The method of claim 17, wherein the mixture comprises from about 1% to about 50% by weight of the single wall carbon nanotube particles.

19. The method of claim 17, comprising cooling the balloon wall region to less than about 0° C.

20. The method of claim 17, further comprising contacting the balloon outer surface to a body vessel.

21. The method of claim 17, wherein at least some the nanotube particles contact other nanotube particles across a cross-sectional thickness of the balloon wall region.

22. The method of claim 17, wherein the one or more fibers are spaced about the circumference of the balloon.

23. The method of claim 17, wherein the one or more fibers include nanoparticles.

24. The method of claim 23, wherein the one or more fibers include single wall carbon nanotubes.

* * * * *